(12) United States Patent
Kim

(10) Patent No.: US 8,971,999 B2
(45) Date of Patent: Mar. 3, 2015

(54) INTRA-ORAL SCANNER

(76) Inventor: Jin Hwan Kim, Seoul (KR)

(*) Notice: Subject to any disclaimer, the term of this patent is extended or adjusted under 35 U.S.C. 154(b) by 221 days.

(21) Appl. No.: 13/515,812

(22) PCT Filed: Dec. 15, 2010

(86) PCT No.: PCT/KR2010/008963
§ 371 (c)(1),
(2), (4) Date: Jun. 14, 2012

(87) PCT Pub. No.: WO2011/074867
PCT Pub. Date: Jun. 23, 2011

(65) Prior Publication Data
US 2012/0295217 A1   Nov. 22, 2012

(30) Foreign Application Priority Data

Dec. 15, 2009  (KR) .................. 10-2009-0124780

(51) Int. Cl.
*A61B 5/05* (2006.01)
*A61B 5/00* (2006.01)
*A61C 9/00* (2006.01)
*A61B 6/14* (2006.01)

(52) U.S. Cl.
CPC ............ *A61B 5/0088* (2013.01); *A61B 5/0062* (2013.01); *A61C 9/0053* (2013.01); *A61B 6/145* (2013.01)
USPC ........................................... 600/476; 433/29

(58) Field of Classification Search
CPC .................................................. A61B 5/0088
USPC .......................................... 600/476; 433/29
See application file for complete search history.

(56) References Cited

U.S. PATENT DOCUMENTS

| | | |
|---|---|---|
| 5,424,836 A | 6/1995 | Weise et al. |
| 2004/0254476 A1 | 12/2004 | Quadling et al. |
| 2006/0154198 A1 | 7/2006 | Durbin et al. |
| 2009/0079993 A1* | 3/2009 | Yatagai et al. ............... 356/497 |
| 2009/0279103 A1 | 11/2009 | Thiel et al. |

FOREIGN PATENT DOCUMENTS

| | | |
|---|---|---|
| DE | 102007005625 A1 | 8/2008 |
| KR | 10-2003-0008826 A | 1/2003 |

(Continued)

OTHER PUBLICATIONS

International Search Report of PCT/KR2010/008963 dated Jul. 27, 2011.

(Continued)

*Primary Examiner* — Jonathan Cwern
(74) *Attorney, Agent, or Firm* — Lee Patent International

(57) ABSTRACT

An intra-oral scanner includes an optical output unit; an optical output control unit to rotate the optical output unit along a first reference axis or moves the optical output unit so as to control an emission position of the output light; an optical system to reflect the output light with the emission position controlled by the optical output control unit to a tooth or teeth being scanned; an optical system driving unit to rotate the optical system along a second reference axis so as to control a reflection angle of the output light; a guide; an optical sensing unit to sense the light reflected by the optical system and convert the sensed light into an electrical signal; and a data transmitting unit to transmit information to a three-dimensional data generating unit to generate a three-dimensional scanning model for the tooth or teeth being scanned.

8 Claims, 6 Drawing Sheets

(56) References Cited

FOREIGN PATENT DOCUMENTS

| KR | 10-2004-0001698 A | 1/2004 |
| KR | 10-2005-0101010 A | 10/2005 |
| KR | 10-2010-0008256 A | 1/2010 |
| WO | 2009/063087 A2 | 5/2009 |

OTHER PUBLICATIONS

European Search Report for EP application No. 10837863.9.

* cited by examiner

INTRA-ORAL SCANNER

This application claims priority to Korean Patent Application No. 10-2009-0124780 filed on Dec. 15, 2009, which is incorporated herein by reference in their entirety.

TECHNICAL FIELD

The present disclosure relates to an intra-oral scanner, in particular, to an intra-oral scanner, which is inserted into a patient's oral cavity to scan the patient's teeth.

BACKGROUND ART

In general, dental hospitals or the like have performed medical cures and treatments to patients' affected parts through impression taking that prepares plaster casts for the patients' teeth. However, in the impression taking process, there have been problems, e.g., consumption of materials, cross-infection, possibility of damage to prepared casts, and preservation difficulties.

As a conventional method widely used to see the state of a patient's oral cavity, there has been a method of inserting a sheet-shaped film into the patient's oral cavity, fixing the film in the proximity of the patient's affected part by using the patient's hand or tongue, projecting a radiation ray such as an X-ray onto the affected part of the oral cavity, and using the film obtained from the projection.

However, since the conventional method depends on measurement through two-dimensional manual works using radiographs, or computer tomography (CT), errors may occur in the process of two-dimensional plane measurement of a three-dimensional structure. Further, a large amount of radiation rays are projected to a patient. Patients would have a financial burden. Complicated trial stages may cause various critical problems.

Accordingly, there has been a demand for an intra-oral scanner, which reduces the possibility of causing any problems in patients' physical conditions and exactly accomplishes three-dimensional modeling of patients' teeth.

DISCLOSURE OF THE INVENTION

Problems to be Solved by the Invention

In an illustrative embodiment, there is provided an intra-oral scanner, which is inserted into a user's oral cavity in a contactless manner to scan the user's teeth and generates three-dimensional scanning model.

Means for Solving the Problems

In accordance with an example of an illustrative embodiment, there is provided an intra-oral scanner including: an optical output unit, which outputs an output light; an optical output control unit, which rotates the optical output unit along a first reference axis or moves the optical output unit in left and right directions so as to control an emission position of the output light; an optical system, which reflects the output light with the emission position controlled by the optical output control unit to a tooth or teeth being scanned; an optical system driving unit, which rotates the optical system along a second reference axis vertical to the first reference axis so as to control a reflection angle of the output light; a guide, which guide the optical system to move within a preset distance from the optical output unit; an optical sensing unit, which senses the light reflected by the optical system at the tooth or teeth being scanned and converts the sensed light into an electrical signal; and a data transmitting unit, which transmits information of the electrical signal, information of the emission position of light and information of the reflection angle to a three-dimensional data generating unit to generate three-dimensional scanning model for the tooth or teeth being scanned.

In accordance with an example of an illustrative embodiment, there is provided an intra-oral scanner including: an optical output unit, which outputs an output light; a first optical system, which reflects the output light outputted from the optical output unit; a second optical system, which reflects the output light reflected through the first optical system to a tooth or teeth being scanned; a first optical system driving unit, which rotates the first optical system along a first reference axis or moves the first optical system in left and right directions so as to control an emission position of the output light; a second optical system driving unit, which rotates the second optical system along a second reference axis vertical to the first reference axis so as to control a reflection angle of the output light; a guide, which guides the second optical system to move within a preset distance from the optical output unit; an optical sensing unit, which senses the light reflected by the second optical system at the tooth or teeth being scanned and converts the sensed light into an electrical signal; and a data transmitting unit, which transmits information of the electrical signal, information of the emission position of light and information of the reflection angle to a three-dimensional data generating unit to generate three-dimensional scanning model for the teeth being scanned.

Effect of the Invention

With the above-described technical means of the illustrative embodiment, the intra-oral scanner is inserted into a patient's oral cavity to scan the patient's teeth in a contactless manner. Thus, three-dimensional data for the patient's teeth can be exactly measured.

With the above-described technical means of the illustrative embodiment, three-dimensional scanning is accomplished by using a light source that does not adversely affect the human body. Thus, patients' teeth can be scanned without affecting the patients' health.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

BEST MODE FOR CARRYING OUT THE INVENTION

Figure 1:
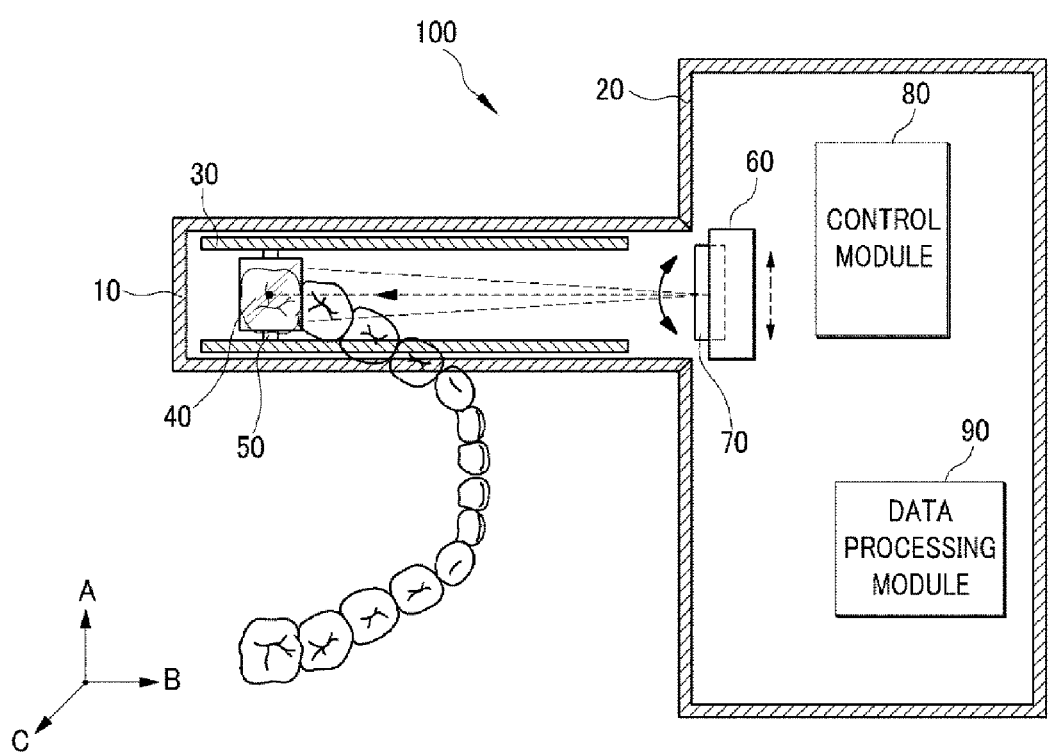
FIG. 1 is a plane view of an intra-oral scanner in accordance with an illustrative embodiment.

Hereinafter, illustrative embodiments will be described in detail with reference to the accompanying drawings so that inventive concept may be readily implemented by those skilled in the art. However, it is to be noted that the present disclosure is not limited to the illustrative embodiments and can be realized in various other ways. In the drawings, certain parts not directly relevant to the descriptions of the present disclosure are omitted to enhance the clarity of the drawings. Throughout this document, like reference numerals denote like parts.

FIG. 1 is a plane view of an intra-oral scanner in accordance with an illustrative embodiment.

Figure 2:
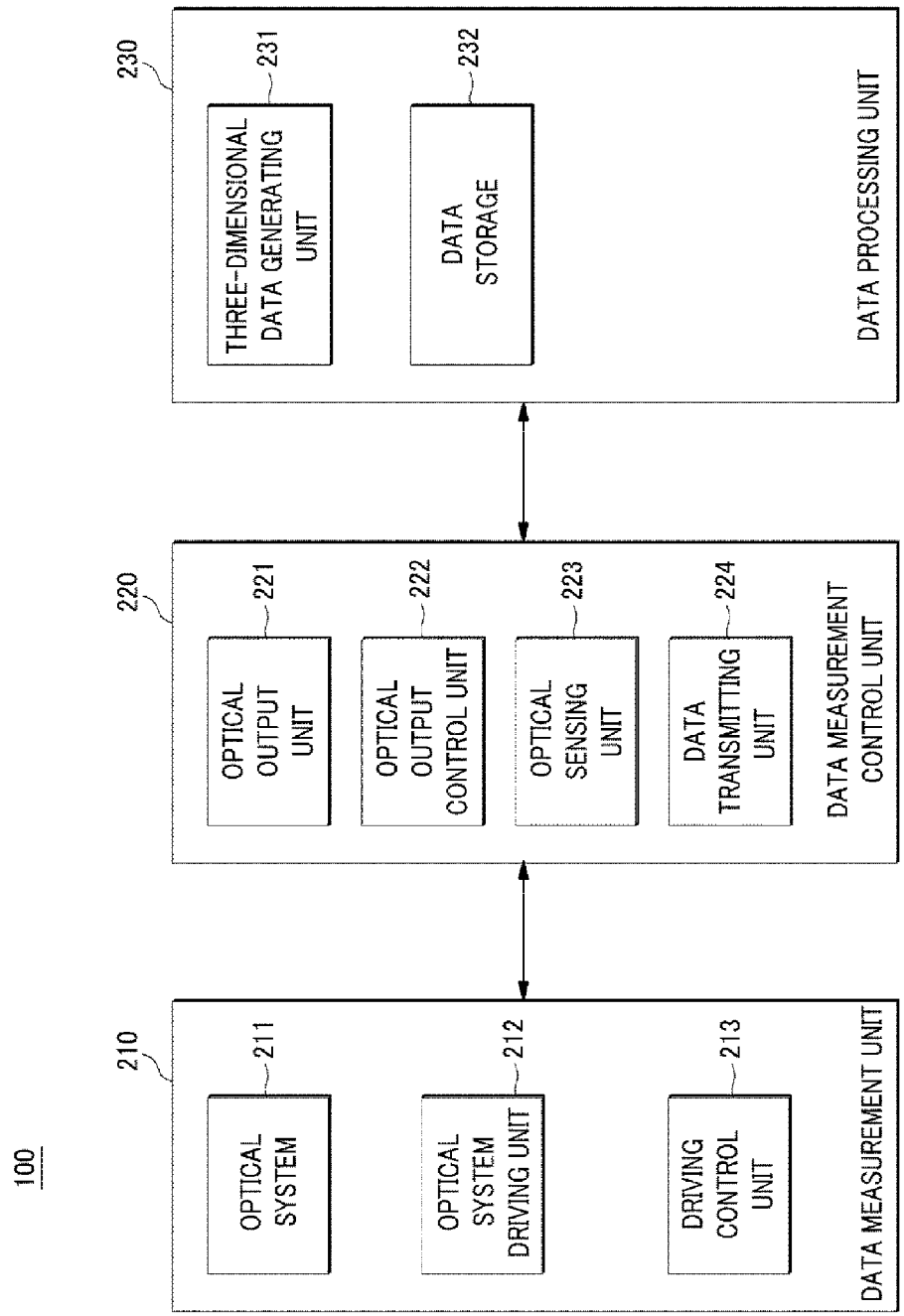
FIG. 2 is a block diagram showing configuration of an intra-oral scanner in accordance with an illustrative embodiment.

FIG. 2 is a block diagram showing configuration of an intra-oral scanner in accordance with an illustrative embodiment.

Figure 3:
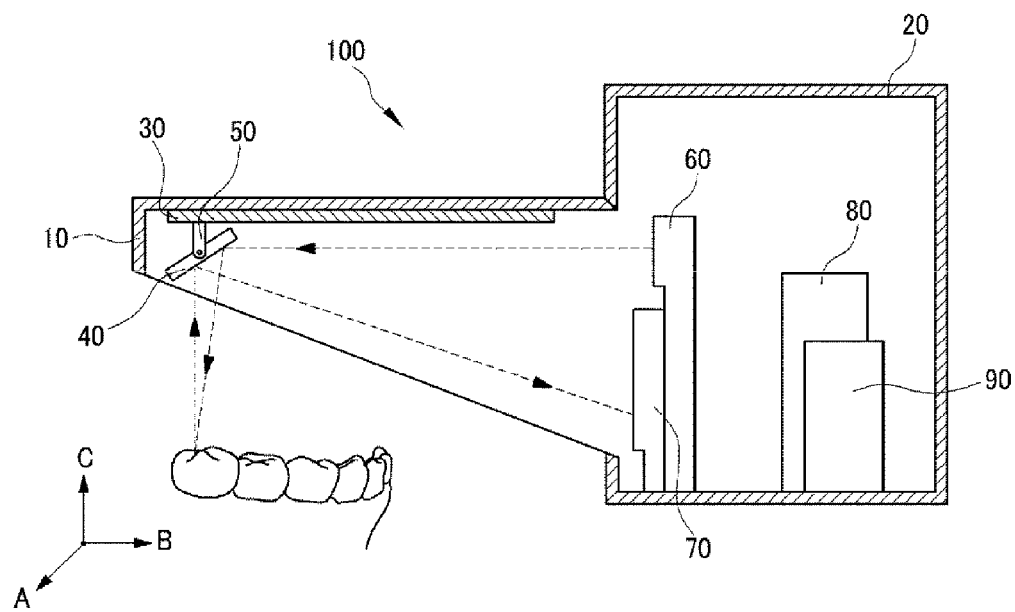
FIG. 3 is a side view of an intra-oral scanner in accordance with an illustrative embodiment.

FIG. 3 is a side view of an intra-oral scanner in accordance with an illustrative embodiment.

As illustrated in FIGS. 1 and 3, an intra-oral scanner 100 in accordance with an illustrative embodiment includes an insertion body 10, a body 20, a guide 30, an optical system 40, an optical system driving member 50, an optical output device 60, an optical sensing device 70, a control module 80, and a data processing module 90.

A frame of the insertion body 10 is in a shape of an insertion tube projected from the body 20 so as to be inserted into the user's oral cavity. The frame may have five surfaces, which include one top surface, two side surfaces, one front surface, and one bottom surface.

The bottom surface of the insertion body 10 includes a light transmission window, which enables a scanning light source (e.g., a "laser light" in an illustrative embodiment) to be projected onto the tooth or teeth.

The top surface of the insertion body 10 is in parallel with the direction that the insertion body 10 is inserted into the oral cavity. The bottom surface has a certain angle to the top surface. Accordingly, the two surfaces may be formed to become large as they are close to the body 20. This configuration is intended to protect light sources by securing a heading path of a light source outputted to the optical system 40 through the inside of the insertion body 10 and a light source reflected from the tooth or teeth and incident to the optical sensing device 70 through the optical system 40.

In the inside of the insertion body 10, the optical system 40 is connected to the guide 30 through the optical system driving member 50 such that the optical system 40 reflects a light source (hereinafter, referred to as "output light") outputted from the optical output device 60 to be projected to the tooth or teeth and reflects an incident light source reflected from the tooth or teeth (hereinafter, referred to as "incident light") to the optical sensing device 70.

In this case, the guide 30 supports the optical system 40 to be connected to the inside of the insertion body 10. The guide 30 controls a rolling member (not illustrated) connected to a motor (not illustrated) or others under a command from the control module 80 to move the optical system 40 forwardly and backwardly in the horizontal direction that the insertion body 10 is inserted. The optical system driving member 50 rotates the optical system 40 along a first reference axis under a command from the control module 80 so as to change an emission angle of the output light. The first reference axis is consistent with an A axis illustrated in FIG. 1.

Provided in the inside of the body 20 are the optical output device 60, the optical sensing device 70, the control module 80, and the data processing module 90. The optical output device 60 outputs a light source to the optical system 40. The optical sensing device 70 receives a light source reflected from the optical system 40. The control module 80 controls driving of each of the optical system 40 and the optical output device 60 and processes output data of the optical sensing device 70. The data processing module 90 generates three-dimensional data by using the data processed through the control module 80.

The optical output device 60 in accordance with an illustrative embodiment is rotated based on a second reference axis so as to change an emission angle of the output light. The second reference axis is vertical to the first reference axis and consistent with a C axis illustrated in FIG. 1. The optical output device 60 moves in left and right directions (i.e., the A axis in FIG. 1) in a sliding manner so as to change an emission position of the output light.

In an illustrative embodiment, a laser diode is described as an example of the optical output device 60. For restriction of a size, an optical output device, which is as small as possible, may be used. The optical sensing device 70 may be a light receiving device such as a charged coupled device (CCD) or a position sensitive device (PSD). In an illustrative embodiment, a PSD is described as an example of the optical sensing device 70.

Hereinafter, a teeth modeling method through three-dimensional scanning by the intra-oral scanner 100 in accordance with an illustrative embodiment will be described with reference to FIGS. 2 and 3.

With respect to the configuration of the intra-oral scanner 100 in accordance with an illustrative embodiment in FIGS. 1 and 3, FIG. 2 illustrates a block diagram for a data measurement unit 210, a data measurement control unit 220, and a data processing unit 230 based on data to be processed.

The configuration units in accordance with an illustrative embodiment in FIG. 2 mean software configuration units or hardware configuration units such as field programmable gate array (FPGA) or application specific integrated circuit (ASIC), and execute their certain functions.

However, the "configuration units" are not limited to software or hardware. Each of the configuration units may be configured to be in a storage medium that can be addressed or configured to play one or more processers.

For example, the configuration units may include configuration units such as software configuration units, object-oriented software configuration units, class configuration units, and task configuration units, processes, functions, properties, procedures, sub-routines, segments of a program code, drivers, firmware, micro codes, circuits, data, database, data structures, tables, arrays, and variables.

The configuration units and functions provided in the corresponding configuration units may be combined to be a less number of configuration units or further divided into additional configuration units.

In this case, the optical system 211 and the optical system driving unit 212 of the data measurement unit 210 are the same in concept as the optical system 40 and the optical system driving member 50 illustrated in FIGS. 1 and 3. The driving control unit 213 includes the partial or whole configuration of the control module 80 illustrated in FIGS. 1 and 3.

The optical output unit 221 and the optical sensing unit 223 of the data measurement control unit 220 are the same in concept as the optical output device 60 and the optical sensing device 70 illustrated in FIGS. 1 and 3. The optical output control unit 222 includes the partial or whole configuration of the control module 80 illustrated in FIGS. 1 and 3. The data transmitting unit 224 of the data measurement control unit 220 is the same in concept as the data processing module 80 illustrated in FIGS. 1 and 3.

The data processing unit 230 illustrated in FIG. 2 generates three-dimensional scanning model for the tooth or teeth being scanned by using data outputted from the data transmitting unit 224. The data processing unit 230 may be included in the inside of the intra-oral scanner 100 in accordance with an illustrative embodiment or connected as a separate apparatus to the intra-oral scanner 100 through cables or the like. For restriction of a size of the intra-oral scanner 100 in accordance with an illustrative embodiment, FIGS. 1 and 3 illustrate that the data processing unit 230 is provided outside.

In the intra-oral scanner 100 in accordance with an illustrative embodiment, the optical output unit 221 outputs the output light (i.e., a laser light source) toward the optical system 211 to correspond to the emission angle or the emission position set under the control of the optical output control unit 222. Based on a value for the emission angle or the emission position controlled by the optical output control unit 222, an A axis coordinate value for the output light projected to the tooth or teeth being scanned can be calculated.

In this case, the optical system 211 is in the state of being rotated based on an emission angle set in accordance with driving of the optical system driving unit 212. Specifically, the driving control unit 213 moves the optical system 211 forwardly and backwardly in the horizontal direction depending on positions of the tooth or teeth being scanned, and rotates the optical system 211 by driving the optical system driving unit 212 in accordance with a rotation angle set in correspondence with parts to be scanned. In this case, based on a value for the rotation angle controlled by the driving control unit 213, a B axis coordinate value for the output light projected to the tooth or teeth being scanned can be calculated.

Thereafter, the output light reflected through the optical system 211 is reflected from the tooth or teeth being scanned and incident again to the optical system 211. The incident light is reflected through the optical system 211 and incident to the optical sensing unit 223.

As illustrated in FIG. 3, the output light outputted from the optical output device 60 is reflected on the optical system 40 and projected to the tooth or teeth being scanned. The light reflected from the tooth or teeth being scanned is reflected again on the optical system 40 and incident on the optical sensing device 70.

In this case, the optical sensing device 70 in accordance with an illustrative embodiment is a PSD device and generates an electrical signal depending on a position to which the incident light is inputted. That is, the optical sensing unit 223 generates position information corresponding to the generated electrical signal. The position information is a height of each of the tooth or teeth parts being scanned. In this case, a C axis coordinate value for the output light projected to the tooth or teeth being scanned can be calculated based on a value for the height sensed by the optical sensing unit 223.

A PSD sensor included in the optical sensing unit 223 in accordance with an illustrative embodiment is an optical electronic sensor and has a structure, in which when an optical spot is formed on a surface, an optical current proportional to an optical energy is generated at an incidence spot and flows toward electrodes of both ends.

The optical sensing unit 223 in accordance with an illustrative embodiment can calculate the C axis coordinate value according to a potential measurement method using an optical triangulation method. The optical triangulation method is a potential measurement method using a two-dimensional triangulation method based on geometric optics. In the optical triangulation method, an optical system exists within one plane surface and is configured based on two optical axises being intersected with each other at an angle of $\theta$.

One of the two optical axises is a condensing optical axis that forms an optical spot on a surface of an object to be measured. The other of the two optical axises is an image optical axis that transmits an image of the optical spot to the light receiving device. Here, the optical spot formed on the surface of the object to be measured is moved in a straight line on the condensing optical axis as a relative position of the object to be measured is changed. In this case, the scope of the movement refers to object trajectory. As the optical spot moves, image viscosity on the light receiving device also moves. The scope of the movement of the image spot refer to image trajectory. The image trajectory has an angle of $\phi$ to a vertical direction of the image optical axis.

In this case, an optical spot movement distance p on the object trajectory and an image spot movement distance q corresponding thereto can be calculated through mathematical formula 1 below.

$$p = \frac{q\cos\phi(s-f)}{f\sin\theta + q\cos\phi\cos\theta} \quad \text{[Mathematical Formula 1]}$$

f is a focal length of an image lens to project an image in accordance with the optical spot to the light receiving device. s is a distance between the image lens and an actual object to be measured.

The angle of $\phi$ can be calculated through mathematical formula 2 below.

$$\phi = \tan^{-1}(f/(s-f)\tan\theta) \quad \text{[Mathematical Formula 2]}$$

If the optical triangulation is applied to an illustrative embodiment, the output light forms an optical spot on the surface of the tooth or teeth being scanned. The light reflected on the tooth or teeth being scanned (i.e., incident light) forms an image on the PSD sensor again. Then, the PSD sensor outputs an electrical signal depending on the image forming position of the incident light. In this case, since the position where an image is formed on the PSD sensor varies depending on variation of the heights of the teeth, values for the heights of the tooth or teeth can be measured.

Subsequently, the data transmitting unit 224 matches the A and B axis coordinate values acquired through the optical output control unit 222 and the driving control unit 213 with the C axis coordinate value acquired from the light sensing unit 223 and transmits the values to the data processing unit 230.

For example, the data transmitting unit 224 calculates the A coordinate value depending on the emission angle or the emission position of the light from the optical output unit 221 controlled by the optical output control unit 222. The data transmitting unit 224 calculates the B coordinate value depending on the emission angle of the optical system 211 controlled by the driving control unit 213. The data transmitting unit 224 calculates the C coordinate value depending on the position of the light incident to the optical sensing unit 223.

The data processing unit 230 generates three-dimensional scanning model for the tooth or teeth being scanned based on input three-dimensional data information.

Specifically, the three-dimensional data generating unit 231 of the data processing unit 230 generates the three-dimensional scanning model for the tooth or teeth being scanned by combining the A, B, and C axis coordinate values received from the data transmitting unit 224 and associated with one another.

The data storage 232 sequentially stores the generated three-dimensional scanning model for the tooth or teeth being scanned in a database or others.

In this case, the intra-oral scanner 100 in accordance with an illustrative embodiment can output the three-dimensional scanning model for the patient's teeth stored in the data storage 232 through a screen provided therein (not illustrated), an output system (not illustrated) connected through data cables, or others.

Figure 4:
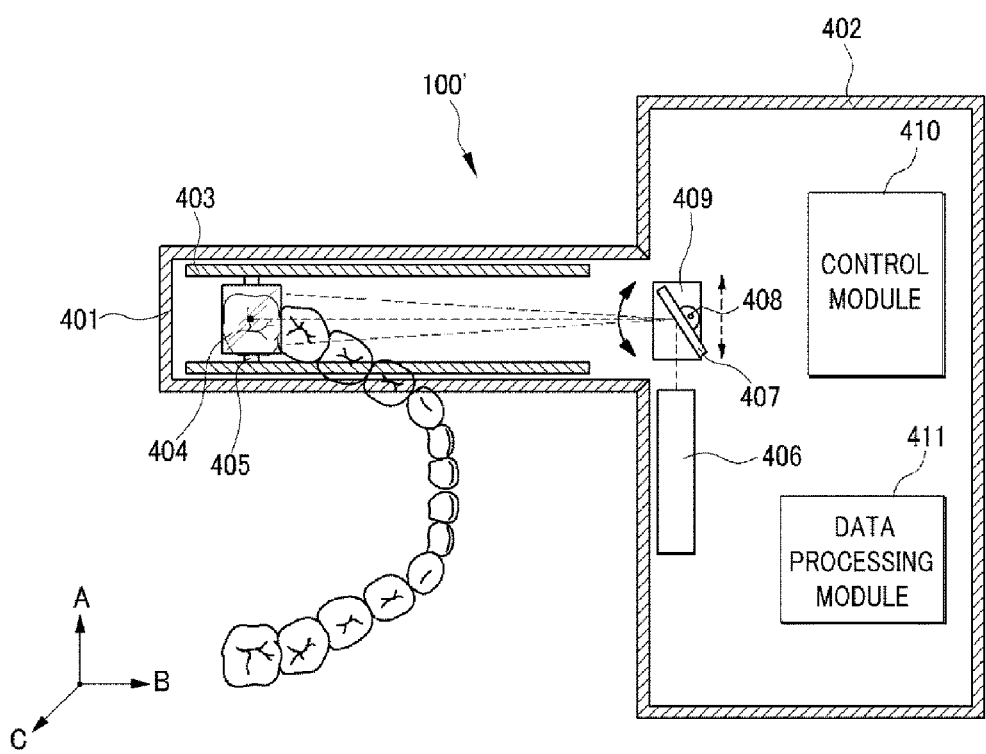
FIG. 4 is a plane view of an intra-oral scanner in accordance with another illustrative embodiment.
Figure 5:
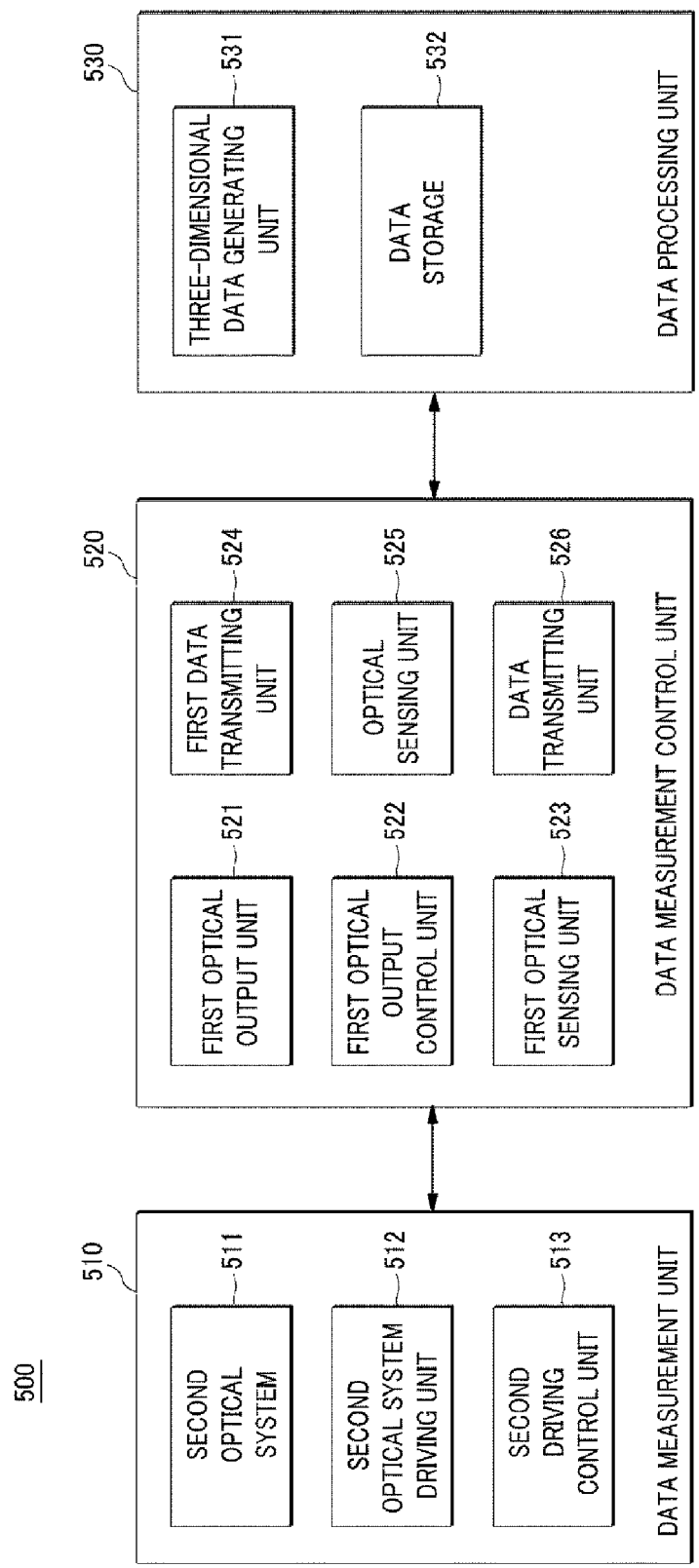
FIG. 5 is a block diagram showing configuration of an intra-oral scanner in accordance with another illustrative embodiment.
Figure 6:
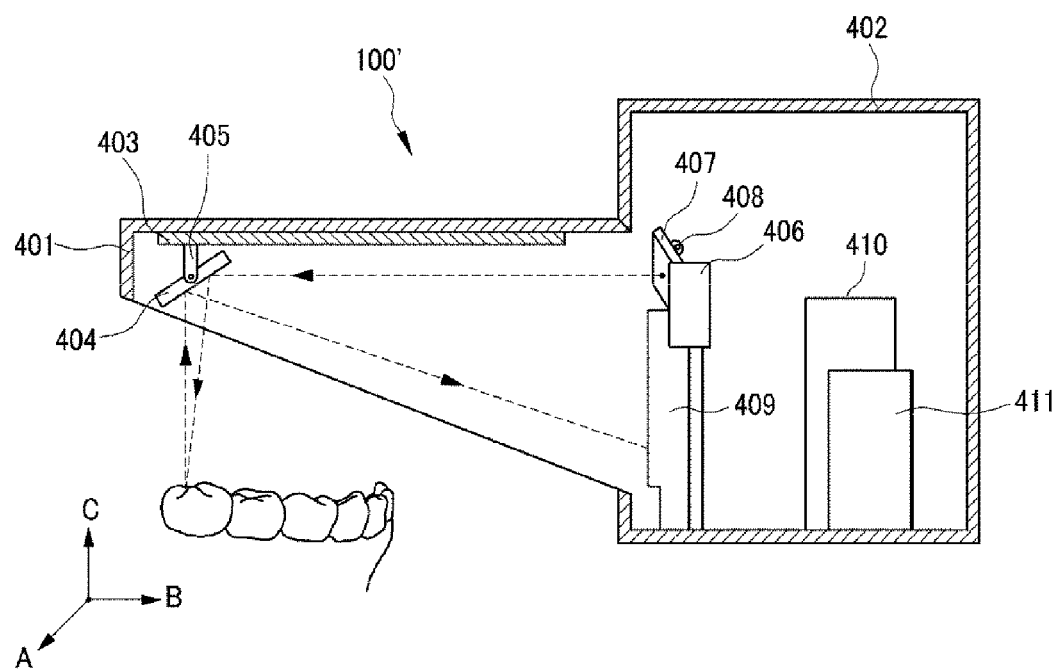
FIG. 6 is a side view of an intra-oral scanner in accordance with another illustrative embodiment.

FIG. 4 is a plane view of an intra-oral scanner in accordance with another illustrative embodiment. FIG. 5 is a block diagram showing configuration of an intra-oral scanner in accordance with another illustrative embodiment. FIG. 6 is a side view of an intra-oral scanner in accordance with another illustrative embodiment.

Unlike the intra-oral scanner 100, the intra-oral scanner 100' in accordance with another illustrative embodiment provides a method of secondarily reflecting the output light to be projected to the tooth or teeth being scanned. For simplification of descriptions, FIGS. 4 to 6 omit detailed descriptions of the configuration units of the intra-oral scanner 100', which are the same as those of the intra-oral scanner 100.

Specifically, as illustrated in FIGS. 4 to 6, the intra-oral scanner 100' in accordance with another illustrative embodiment includes a guide 403, a second optical system 404, and a second optical system driving unit 405 in the inside of an insertion unit 401. The intra-oral scanner 100' includes an optical output device 406, a first optical system 407, a first optical system driving member 408, an optical sensing device 409, a control module 410, and a data processing module 411 in the inside of a body 402.

In this case, the intra-oral scanner 100' in accordance with another illustrative embodiment primarily reflects the output light outputted from the optical output device 406 through the first optical system 407 and outputs the light to the second optical system 404. In this case, the first optical system driving member 408 rotates the first optical system 407 along the second reference axis so as to change an emission angle of the output light. The first optical system driving member 408 moves the first optical system 407 in left and right directions in a sling manner so as to change an emission position of the output light.

Hereinafter, a teeth modeling method through three-dimensional scanning in the intra-oral scanner 100' in accordance with another illustrative embodiment will be described with reference to FIG. 5.

With respect to the configuration of the intra-oral scanner 100' in accordance with another embodiment in FIGS. 4 and 6, FIG. 5 illustrates a block diagram for a data measurement unit 510, a data measurement control unit 520, and a data processing unit 530 based on data to be processed.

The configuration units in accordance with another illustrative embodiment in FIG. 5 mean software configuration units or hardware configuration units such as field programmable gate array (FPGA) or application specific integrated circuit (ASIC), and execute their certain functions. However, the "configuration units" are not limited to software or hardware. Each of the configuration units may be configured to be in a storage medium that can be addressed or configured to play one or more processors.

For example, the configuration units may include configuration units such as software configuration units, object-oriented software configuration units, class configuration units, and task configuration units, processes, functions, properties, procedures, sub-routines, segments of a program code, drivers, firmware, micro codes, circuits, data, database, data structures, tables, arrays, and variables.

The configuration units and functions provided in the corresponding configuration units may be combined to be a less number of configuration units or further divided into additional configuration units.

The second optical system 511 and the second optical system driving unit 512 of the data measurement unit 510 are the same in concept as the second optical system 404 and the second optical driving member 405 illustrated in FIGS. 4 and 6. The second driving control unit 513 includes the partial or whole configuration of the control module 410 illustrated in FIGS. 4 and 6.

The second optical system 511, the second optical system driving unit 512, and the second driving control unit 513 execute the same operations as those of the optical system 211, the optical system driving unit 212, and the driving control unit 213 in accordance with an illustrative embodiment in FIG. 2.

The first optical system 521 and the first optical system driving unit 522 of the data measurement control unit 520 are the same in concept as the first optical system 407, and the first optical system driving member 408 illustrated in FIGS. 4 and 6. The first driving control unit 523 includes the partial or whole configuration of the control module 410.

The optical output unit 524 and the optical sensing unit 525 of the data measurement control unit 520 are the same in concept as the optical output device 406 and the optical sensing device 409 illustrated in FIGS. 4 and 6. The data transmitting unit 526 includes the partial or whole configuration of the data processing module 411 illustrated in FIGS. 4 and 6.

Meanwhile, in FIG. 5, the data processing unit 530 generates three-dimensional scanning model for the tooth or teeth being scanned by using data outputted from the data transmitting unit 526. The data processing unit 530 may be included in the intra-oral scanner 100' in accordance with another illustrative embodiment or connected as a separate apparatus to the intra-oral scanner 100' through cables or others. For restriction of a size of the intra-oral scanner 100' in accordance with another illustrative embodiment, FIGS. 4 and 6 illustrates that the data processing unit 530 is provided outside.

The optical sensing unit 525, the data transmitting unit 526, and the data processing unit 530 execute the same operations as those of the optical sensing unit 223, the data transmitting unit 224, and the data processing unit 230 in accordance with an illustrative embodiment in FIG. 2.

First, in the intra-oral scanner 100' in accordance with another illustrative embodiment, an output light (i.e., a laser light) outputted from the optical output unit 524 in a straight line is primarily reflected at the emission angle or the emission position set through the first optical system 521.

Specifically, the first optical system 521 is in the state of being rotated at the set emission angle as the first optical driving unit 522 is driven under control by the first driving control unit 523. Here, the first optical system driving unit 522 rotates the first optical system 521 along the second reference axis under a command from the first driving control unit 523 so as to changes the emission angle of the output light. The second reference axis is consistent with the C axis illustrated in FIG. 4. In this case, the A axis coordinate value for the output light projected to the tooth or teeth being scanned can be calculated based on a value for the emission angle controlled by the first driving control unit 523.

In another illustrative embodiment, the first optical driving system driving unit 522 may move the first optical system 521 in left and right directions in a sliding manner so as to change the emission position of the output light. In this case, the A axis coordinate value for the output light projected to the tooth or teeth being scanned can be calculated based on a value for the emission position controlled by the first driving control unit 523.

The output light reflected through the first optical system 521 is projected to the second optical system 511. The output light is secondarily reflected from the second optical system 511 at the set emission angle and projected to the tooth or teeth being scanned. In this case, the second optical system 511 is in the state of being rotated at the set emission angle as the second optical system driving unit 512 is driven under control by the second driving control unit 513. The second optical system 511 is rotated along the first reference axis. The first reference axis is consistent with the A axis illustrated in FIG. 4. In this case, the B axis coordinate value for the output light projected to the tooth or teeth being scanned can be calculated based on a value for the emission angle controlled by the second driving control unit 513.

Thereafter, the output light reflected through the second optical system 511 is reflected from the tooth or teeth being scanned and incident again to the second optical system 511. The incident light is reflected through the second optical system 511 and incident to the optical sensing unit 525.

That is, as illustrated in FIG. 6, the output light outputted from the optical output device 406 is primarily reflected on the first optical system 407 and projected to the second optical system 404. The output light secondarily reflected on the second optical system 404 is projected to the tooth or teeth being scanned. The incident light reflected from the tooth or teeth being scanned is reflected again on the second optical system and incident to the optical sensing device 409.

Accordingly, the optical sensing unit 525 generates position information corresponding to an electrical signal depending on a position to which the incident light is incident. The position information is a height of each of the tooth or teeth parts being scanned. Based on values of the heights sensed by the optical sensing unit 525, the C axis coordinate value for the output light projected to the tooth or teeth being scanned can be calculated.

Thereafter, the data transmitting unit 526 matches the A and B axis coordinate values acquired through the first driving control unit 523 and the second driving control unit 513 with the C axis coordinate value acquired from the optical sensing unit 523 and transmits the values to the data processing unit 530.

The data processing unit 530 generates three-dimensional scanning model for the tooth or teeth being scanned based on the input three-dimensional data information.

Specifically, the three-dimensional data generating unit 531 of the data processing unit 530 generates the three-dimensional scanning model for the tooth or teeth being scanned by combining the A, B, C axis coordinate values received from the data transmitting unit 526 and associated with one another.

The data storage 532 sequentially stores the generated three-dimensional scanning model for the tooth or teeth being scanned in a database or others.

The apparatus and the system of the illustrative embodiment have been described in relation to the certain examples. However, the components or parts or all the operations of the apparatus and the system may be embodied using a computer system having universally used hardware architecture. The above description of the illustrative embodiments is provided for the purpose of illustration, and it would be understood by those skilled in the art that various changes and modifications may be made without changing technical conception and essential features of the illustrative embodiments. Thus, it is clear that the above-described illustrative embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

What is claimed is:

1. An intra-oral scanner comprising:
   an optical output unit configured to output an output light;
   an optical output control unit configured to rotate the optical output unit along a first reference axis or to move the optical output unit along a sliding direction parallel to a second reference axis vertical to the first reference axis so as to control an emission position of the output light;
   an optical system configured to reflect the output light with the emission position controlled by the optical output control unit to a tooth or teeth being scanned;
   an optical system driving unit configured to rotate the optical system along the second reference axis so as to control a reflection angle of the output light;
   a guide configured to guide the optical system to move within a preset distance from the optical output unit;
   an optical sensing unit configured to sense the light reflected by the optical system at the tooth or teeth being scanned and to convert the sensed light into an electrical signal;
   a data transmitting unit configured to transmit information of the electrical signal, information of the emission position of light and information of the reflection angle to a three-dimensional data generating unit to generate a three-dimensional scanning model for the tooth or teeth being scanned; and
   an insertion body configured to include the guide, the optical system and the optical system driving unit to guide the intra-oral scanner to be inserted into an oral cavity and to secure a heading path of the output light and the light reflected by the optical system,
   wherein the insertion body includes a top surface perpendicular to the first reference axis that is in parallel with a direction of being inserted into the oral cavity;
   a bottom surface having a predetermined angle to the top surface so as to secure a heading path of the output light and the light reflected by the optical system; and
   an optical transmission window, which enables the output light reflected by the optical system to head to the tooth or teeth being scanned, and the light reflected at the tooth or teeth being scanned to head to the optical system, and
   wherein the optical output control unit controls the emission position of the output light so as to enable the output light outputted from the optical output unit to head to the optical system along a normal direction of the both first and second reference axes,
   wherein the guide is connected to the top surface of the insertion body and enables the optical system to translate along the normal direction of the both first and second reference axes, and wherein the optical system reflects the output light that is reflected at the teeth or tooth and transmitted through the optical transmission window to the optical sensing unit.

2. The intra-oral scanner of claim 1, wherein the data transmitting unit transmits a B axis coordinate determined depending on the reflection angle, an A axis coordinate determined depending on the emission position, and a C axis coordinate determined depending on a height of the tooth or teeth being scanned, determined in accordance with the electrical signal.

3. The intra-oral scanner of claim 1, wherein the optical sensing unit determines a value for the electrical signal depending on where the light reflected by the optical system at the tooth or teeth being scanned is incident to an optical sensing device, and generates a value for a C axis coordinate in accordance with a value for the height of the tooth or teeth being scanned.

4. The intra-oral scanner of claim 1, wherein the first reference axis is the same as a C axis for the three-dimensional scanning model, the second reference axis is the same as an A axis for the three-dimensional scanning model, and the A and C axes are vertical to each other.

5. An intra-oral scanner comprising:
an optical output unit configured to output an output light;
a first optical system configured to reflect the output light outputted from the optical output unit;
a second optical system configured to reflect the output light reflected through the first optical system to a tooth or teeth being scanned;
a first optical system driving unit configured to rotate the first optical system along a first reference axis or to move the first optical system along a sliding direction parallel to a second reference axis vertical to the first reference so as to control an emission position of the output light;
a second optical system driving unit configured to rotate the second optical system along the second reference axis vertical so as to control a reflection angle of the output light;
a guide configured to guide the second optical system to move within a preset distance from the optical output unit;
an optical sensing unit configured to sense the light reflected by the second optical system at the tooth or teeth being scanned and to convert the sensed light into an electrical signal;
a data transmitting unit configured to transmit information of the electrical signal, information of the emission position of light and information of the reflection angle to a three-dimensional data generating unit to generate a three-dimensional scanning model for the teeth being scanned; and
an insertion body configured to include the guide, the second optical system and the second optical system driving unit to guide the intra-oral scanner to be inserted into an oral cavity and to secure a heading path of the output light and the light reflected by the second optical system,
wherein the insertion body includes a top surface perpendicular to the first reference axis that is in parallel with a direction of being inserted into the oral cavity;
a bottom surface having a predetermined angle to the top surface so as to secure a heading path of the output light and the light reflected by the second optical system; and
an optical transmission window, which enables the output light reflected by the second optical system to head to the tooth or teeth being scanned, and the light reflected at the tooth or teeth being scanned to head to the second optical system, and
wherein the first optical output control unit controls the emission position of the output light so as to enable the output light outputted from the optical output unit to head to the optical system along a normal direction of the both first and second reference axes,
wherein the guide is connected to the top surface of the insertion body and enables the optical system to translate along the normal direction of the both first and second reference axes, and
wherein the first optical system driving unit controls the emission position of the output light so as to enable the output light outputted from the optical output unit to head to the second optical system along a normal direction of the both first and second reference axes,
wherein the guide is connected to the top surface of the insertion body and enables the second optical system to translate along the normal direction of the both first and second reference axes, and
wherein the second optical system reflects the output light that is reflected at the teeth or tooth and transmitted through the optical transmission window to the optical sensing unit.

6. The intra-oral scanner of claim 5, wherein the data transmitting unit transmits a B axis coordinate determined depending on the reflection angle, an A axis coordinate determined depending on the emission position, and a C axis coordinate determined depending on a height of the tooth or teeth being scanned, determined in accordance with the electrical signal.

7. The intra-oral scanner of claim 5, wherein the optical sensing unit determines a value for the electrical signal depending on where the light reflected by the second optical system is incident to an optical sensing device, and generates a C axis coordinate value corresponding to the value for the electrical signal.

8. The intra-oral scanner of claim 5, wherein the first reference axis is the same as a C axis for the three-dimensional scanning model, the second reference axis is the same as an A axis for the three-dimensional scanning model, and the A and C axes are vertical to each other.

* * * * *